United States Patent
Bossi et al.

(10) Patent No.: US 10,521,560 B2
(45) Date of Patent: Dec. 31, 2019

(54) METHOD AND SYSTEM FOR REMOTE MEDICATION MANAGEMENT, AUDIT AND COMPLIANCE SYSTEM

(71) Applicant: INRange Systems, Inc., Erie, PA (US)

(72) Inventors: Christopher E. Bossi, Altoona, PA (US); Bruce Allan Moser, Jr., Bellwood, PA (US)

(73) Assignee: INRANGE SYSTEMS, INC., Erie, PA (US)

( * ) Notice: Subject to any disclaimer, the term of this patent is extended or adjusted under 35 U.S.C. 154(b) by 471 days.

(21) Appl. No.: 15/364,784

(22) Filed: Nov. 30, 2016

(65) Prior Publication Data

US 2018/0150613 A1     May 31, 2018

(51) Int. Cl.
*G06F 19/00*     (2018.01)
*G06F 16/22*     (2019.01)
(Continued)

(52) U.S. Cl.
CPC .......... *G06F 19/3456* (2013.01); *G06F 16/22* (2019.01); *G06F 16/2358* (2019.01);
(Continued)

(58) Field of Classification Search
CPC ...... G16H 40/67; G16H 20/13; G06Q 10/087; G06Q 50/22; G06F 19/3456; G06F 16/2358; G06F 16/22; G06F 19/3462
See application file for complete search history.

(56) References Cited

U.S. PATENT DOCUMENTS

| 5,014,875 A | * | 5/1991 | McLaughlin ....... G07F 17/0092 221/122 |
| 2003/0025590 A1 | | 2/2003 | Gokcebay et al. |

(Continued)

FOREIGN PATENT DOCUMENTS

WO    2007/112413 A2    10/2007

OTHER PUBLICATIONS

Notification of Transmittal of the International Search Report and the Written Opinion of the International Searching Authority (Forms PCT/ISA/220, PCT/ISA/210 and PCT/ISA/237) dated Mar. 19, 2018, by the Korean Intellectual Property Office in corresponding International Application No. PCT/US2017/063951. (12 pages).

(Continued)

*Primary Examiner* — Christopher L Gilligan
(74) *Attorney, Agent, or Firm* — Buchanan Ingersoll & Rooney PC (57) ABSTRACT

A remote medication management system for monitoring remote access to medication interfaced with a medication dispensing apparatus includes: a container database configured to store container records related to physical containers stored in the medication dispensing apparatus, each including inventory data entries related to medication stored therein, each inventory data entry including a medication identifier; an input device configured to receive a specific medication identifier; a detection module configured to detect access to a specific physical container stored in the medication dispensing apparatus; a querying module configured to identify a specific container record related to the accessed specific physical container; a determination module configured to determine that the specific medication identifier is not included in any of the inventory data entries included in the identified specific container record; and a (Continued)

memory configured to store a data entry in an event log related to the access to the specific physical container.

16 Claims, 5 Drawing Sheets

(51) Int. Cl.
  *G06F 16/23* (2019.01)
  *G06Q 10/08* (2012.01)
  *G16H 40/67* (2018.01)
  *G16H 20/13* (2018.01)
(52) U.S. Cl.
  CPC ........... *G06Q 10/087* (2013.01); *G16H 20/13* (2018.01); *G16H 40/67* (2018.01)

(56) References Cited

U.S. PATENT DOCUMENTS

| | | |
|---|---|---|
| 2003/0205953 A1 | 11/2003 | Fox |
| 2007/0050051 A1 | 3/2007 | Chang |
| 2007/0171060 A1 | 7/2007 | Trent et al. |
| 2013/0006652 A1* | 1/2013 | Vahlberg .............. G06Q 10/087 705/2 |
| 2013/0282392 A1* | 10/2013 | Wurm .................... G06Q 50/22 705/2 |
| 2016/0022542 A1* | 1/2016 | Lehmann ............ G06F 19/3462 206/534 |

OTHER PUBLICATIONS

"Maximize Medication, Security, Availability and Predictability," Safe Medication Administration, CUBEtm System—BD, Dec. 6, 2016, pp. 1-2, Becton, Dickinson and Company.
"StatSafe Medication Management," Phoenix LTC—StatSafe Medication Management, Dec. 6, 2016, pp. 1-5, Phoenix LTC and the Bergmann Group, Phoenix, Arizona.
"Automation Systems," OmniRx TT, pp. 1, Omnicell, Inc., Mountain View, CA.
"Imediate Access," PharMerica, Dec. 6, 2016, pp. 1-3.
"Touchpoint Medical Products," Dec. 6, 2016, pp. 1-2, Ali Group Company.
"FirstDosetm Medication Management System," Capsa Solutions, 2013, pp. 1-6, Capsa Solutions.
Chapman, "Class II Special Controls Guidance Document: Remote Medication Management System," Center for Devices and Radiological Health, Oct. 19, 2007, pp. 1-15.

* cited by examiner

METHOD AND SYSTEM FOR REMOTE MEDICATION MANAGEMENT, AUDIT AND COMPLIANCE SYSTEM

FIELD

The present disclosure relates to remote access of medication and the auditing of access thereto, specifically the use of a remote medication management system and specifically configured to enable access to several physical containers while auditing such access to ensure compliance with appropriate standards and accountability regarding access to and use of stored medications.

BACKGROUND

Remote medication management systems are useful systems that provide for the ability to store medications that are accessed via a computing terminal or other similar interface that implements security measures to prohibit unauthorized access to medications. The result is that medications are stored in a secure manner that can prevent theft and unauthorized usage of medications, as well as cut down on instances where prescriptions may be mixed or incorrect dosages applied during patient care. Many remote medication management systems accomplish such benefits via the use of separated physical containers inside of the remote medication management system.

However, such systems operate by having mechanical locks placed on every physical container inside of the remote medication management system. Such systems are effective at preventing unauthorized access to medications, due to the mechanical locks, where access to any physical container is only allowed following authentication and/or the entering of a valid medication order for medication stored within. However, the use of mechanical locks on every single physical container results in such remote medication management systems being very expensive, which may be unfeasible for some facilities, particularly smaller, independent clinics and pharmacies. In addition, having separate locks on every physical container can make resupply and inventory of the system time consuming and difficult. In some cases, the manufacturer or distributer of the remote medication management system may require locked physical containers to be provided back to them, or to an authorized third party, for resupply of medications, further complicating the process and resulting in additional expenses that may be unfeasible for some facilities.

Thus, there is a need for a remote medication management system that may provide controlled access to medications that can achieve the benefits of traditional remote medication management systems, particularly the prevention of usage of incorrect medications and controlled access to medication, without the need for mechanical locks to be placed on every physical container.

SUMMARY

The present disclosure provides a description of systems and methods for monitoring remote access to medication in remote medication management systems. The methods and systems discussed herein provide for remote medication management systems that include a plurality of physical containers that are not independently locked, reducing the cost of such systems and increasing accessibility with respect to resupply and inventorying. Alarms and auditing techniques are used to ensure that personnel access the correct medication any time an order is to be fulfilled, while ensuring that any unauthorized access is properly logged to minimize the use of incorrect medications or dosages and to easily identify any theft or other misuse. As a result, the remote medication management systems discussed herein may provide all of the benefits of traditional remote medication management systems, with the added benefit of easier inventorying and resupply, while reducing both the initial and recurring expenses related therewith.

A method for monitoring remote access to medication includes: storing, in a container database of a remote medication management system, a plurality of container records, wherein each container record is related to a physical container stored in a medication dispensing apparatus and includes one or more inventory data entries related to a medication stored in the related physical container, each inventory data entry including at least a medication identifier; receiving, by an input device of the remote medication management system, user credentials associated with a user of the remote medication management system, wherein the user credentials includes at least an identification value; receiving, by an input device of the remote medication management system, a specific medication identifier; detecting, by a detection module of the remote medication management system, access to a specific physical container of a plurality of physical containers stored in the medication dispensing apparatus; executing, by a querying module of the remote medication management system, a query on the container database to identify a specific container record related to the accessed specific physical container; determining, by a determination module of the remote medication management system, that the specific medication identifier is not included in any of the one or more inventory data entries included in the identified specific container record; and storing, in a memory of the remote medication management system, a data entry in an event log related to the access to the specific physical container, wherein the data entry includes at least the identification value included in the user credentials.

A remote medication management system for monitoring remote access to medication interfaced with a medication dispensing apparatus includes: a container database configured to store a plurality of container records, wherein each container record is related to a physical container stored in the medication dispensing apparatus and includes one or more inventory data entries related to a medication stored in the related physical container, each inventory data entry including at least a medication identifier; an input device configured to receive user credentials associated with a user of the remote medication management system, wherein the user credentials includes at least an identification value, and receive a specific medication identifier; a detection module configured to detect access to a specific physical container of a plurality of physical containers stored in the medication dispensing apparatus; a querying module configured to execute a query on the container database to identify a specific container record related to the accessed specific physical container; a determination module configured to determine that the specific medication identifier is not included in any of the one or more inventory data entries included in the identified specific container record; and a memory configured to store a data entry in an event log related to the access to the specific physical container, wherein the data entry includes at least the identification value included in the user credentials.

BRIEF DESCRIPTION OF THE DRAWING FIGURES

The scope of the present disclosure is best understood from the following detailed description of exemplary embodiments when read in conjunction with the accompanying drawings. Included in the drawings are the following figures.

Further areas of applicability of the present disclosure will become apparent from the detailed description provided hereinafter. It should be understood that the detailed description of exemplary embodiments are intended for illustration purposes only and are, therefore, not intended to necessarily limit the scope of the disclosure.

DETAILED DESCRIPTION

System for Monitoring and Auditing of Remote Access to Medication

Figure 1A:
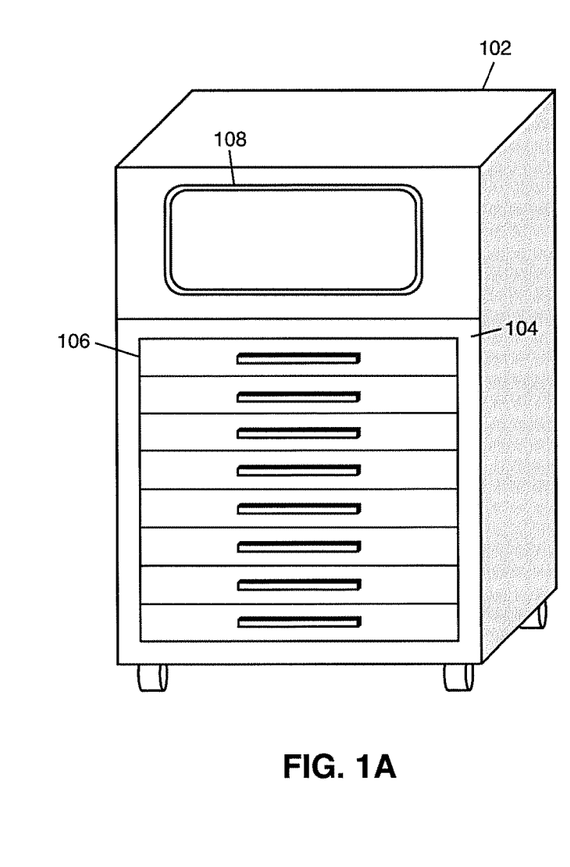
FIG. 1A is a diagram illustrating a remote medication management system for use in storing and distributing medication and the monitoring and auditing of access thereto in accordance with exemplary embodiments.

FIG. 1A illustrates a remote medication management system 102 that may be used for the storage and distribution of medication, where the remote medication management system 102 may be configured to monitor and audit access to such medication for compliance, accountability, and to ensure proper patient care.

The remote medication management system 102, discussed in more detail below with respect to FIG. 2, may be a specifically configured computing system that is configured to interact with a medication dispensing apparatus 104 for the storage and distribution of medication. The medication dispensing apparatus 104 may be comprised of one or more physical compartments 106, here shown as drawers though other configurations such as bin or the like are contemplated. Each physical compartment 106 may be comprised of a plurality of physical containers or compartments 107, also referred to as bins, where each physical container 107 is configured to store one or more medications. As discussed herein, "medication" may refer to both a specific type of medication as well as a specific dosage, such that a single type of medication (e.g., aspirin), whether pill, liquid, injection or other delivery formulation. Further, two different doses of the same drug (e.g., 75 milligrams and 325 milligrams), may be considered two different medications for the purposes discussed herein. For example, a physical container 107 that stores three different dosage amounts for a single type of medication may be considered to store three different medications. Additionally, a container may also hold multiple identical doses of the same medication and no other medications.

Figure 1B:
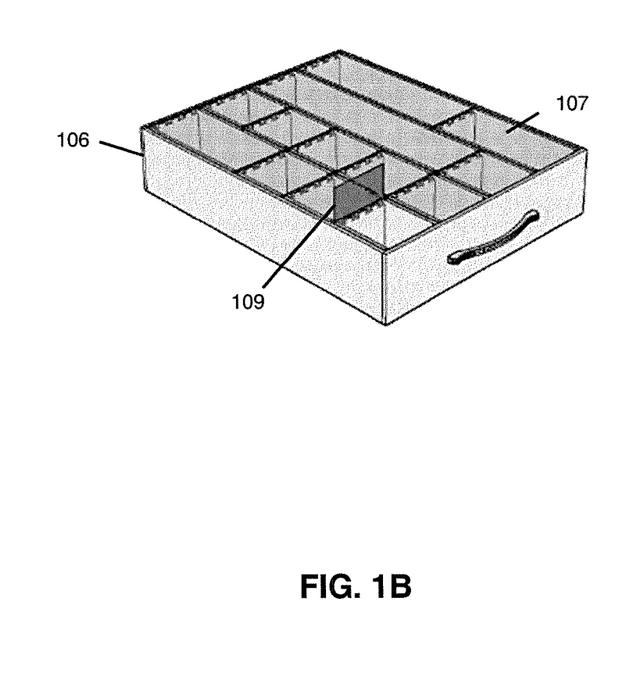
FIG. 1B is a diagram illustrating a containers in the drawers of the remote medication management system of FIG. 1A in accordance with exemplary embodiments.

In some embodiments, the medication dispensing apparatus 104 may include a single physical compartment 106, which may store a plurality of physical containers. In other embodiments, such as the embodiment illustrated in FIG. 1A, the medication dispensing apparatus 104 may include a plurality of physical compartments 106, each of which may store a plurality of physical containers. For instance, in the embodiment illustrated in FIG. 1A, the medication dispensing apparatus 104 may be a cabinet where each physical compartment 106 is a drawer that may slide out from the cabinet, where the physical containers 107 stored therein may be distributed in a two-dimensional array inside of the drawer as shown in FIG. 1B. In such an embodiment, the sizes of the physical containers and distribution in each drawer may vary, such as to accommodate different types and amounts of medication. It will be apparent to persons having skill in the relevant art that the implementation illustrated in FIGS. 1A and 1B of the medication dispensing apparatus 104 is used as illustration only, and that alternative implementations may be suitable for use in conjunction with the methods and systems discussed herein. For example, the medication dispensing apparatus may be a cabinet that opens from the top with a single physical compartment 106 of physical containers arranged two-dimensionally therein. In another example, the medication dispensing apparatus may be a cylinder that rotates, with removable physical compartments situated therein (e.g., in one-third sections of a circle) that include physical containers.

Figure 1C:
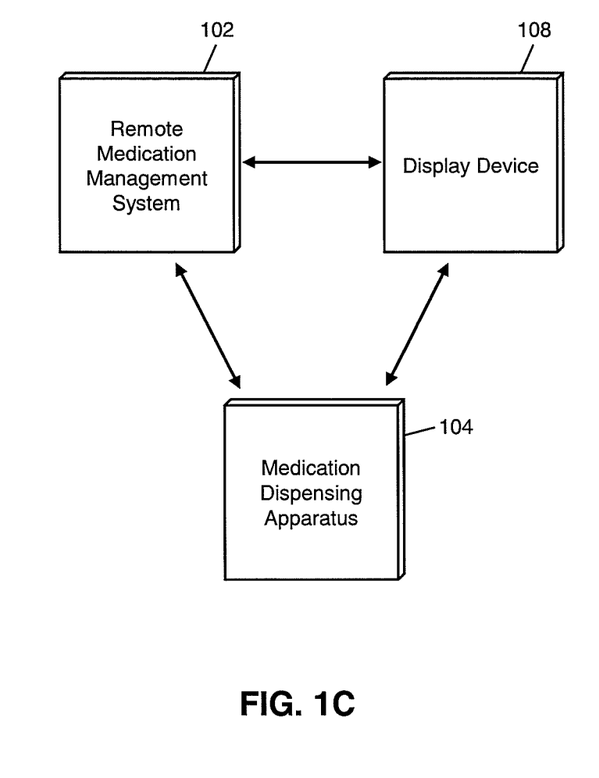
FIG. 1C is a block diagram illustrating a high level system architecture of the remote medication management system in FIG. 1A in accordance with exemplary embodiments.

The remote medication management system 102 may also include a display device 108. As illustrated in FIG. 1A, the display device 108 may be housed in a single housing with the remote medication management system 102, which, in some embodiments, may also include the medication dispensing apparatus 104. It will be apparent to persons having skill in the relevant art that the methods and systems discussed herein may be implemented without the use of a single housing. For instance, FIG. 1C illustrates an architecture of the system that includes the remote medication management system 102, medication dispensing apparatus 104, and display device 108. The methods and systems discussed herein may be implemented such that there is communication between the remote medication management system 102, medication dispensing apparatus 104, and display device 108, even if such devices may be separately housed and, in some cases, located in different physical areas. For example, the remote medication management system 102 may be implemented in a computing device that is located in a separate physical area of a clinic from the medication dispensing apparatus 104. In such an example, both the remote medication management system 102 and medication dispensing apparatus 104 may include a display device 108, and the remote medication management system 102 and medication dispensing apparatus 104 may communicate using a suitable communication network and method, such as via a local area network, wireless area network, radio frequency, Bluetooth, etc. Any type of physical implementation where communication may occur between the remote medication management system 102, medication dispensing apparatus 104, and display devices 108 may be used.

The remote medication management system 102 may be configured to store an inventory of the physical containers stored in the medication dispensing apparatus 104. The inventory may be comprised of a plurality of container records, discussed in more detail below, where each container record is related to a physical container 107 and includes data regarding the medications stored therein. Such data may include a medication identifier (e.g., serial number, Universal Product Code, National Drug Code, registration number, medication name, etc.), quantity, dosage, branding, and any other suitable data related to the medication. A user may access the remote medication management system 102 via a suitable input device (e.g., the display device 108 or any other type of input device interfaced with the remote medication management system 102, as discussed in more detail below) for access to the medication dispensing apparatus 104 and medications stored therein. The user may input an order for medication to the remote medication management system 102, which may identify the physical container 107 that stores such medication by examining the container records, and instruct the medication dispensing apparatus 104 to provide access to the corresponding physical container. For instance, the medication dispensing apparatus 104 may have a lock on the cabinet and/or a lock on the physical compartment 106 that stores the physical container, and may unlock such lock(s) after the order has been entered.

In some embodiments, the remote medication management system 102 may require the user to provide authentication data prior to providing access to a medication. In such embodiments, the remote medication management system 102 may include an input device configured to collect authentication data from the user. Authentication data may include any data uniquely associated with a specific user, such as a username, password, email address, phone number, registration number, identification number, fingerprint, retinal scan, facial scan, vocal identity, palm print, etc. In some cases, the remote medication management system 102 may provide access (e.g., via instructing the medication dispensing apparatus 104 to unlock) to physical containers for every user following authentication, where authentication data may be used for auditing. In other cases, the remote medication management system 102 may store data related to user permissions of physical compartments 106 and/or physical containers 107, where user access to certain physical compartments 106, physical containers, or specific medications may be limited. In such cases, the remote medication management system 102 may authenticate the user based on their supplied authentication data and authentication data registered with the remote medication system 102 (e.g., during a traditional registration process therewith) and may only instruct the medication dispensing apparatus 104 to provide access to a physical container 107 if the user is authorized. In cases where authentication fails or the user may not be authorized to access a requested medication, the remote medication management system 102 may instruct the display device 108 interfaced therewith to display such an indication to the user.

Following the input of the order for medication, and, if applicable, authentication of the user, the medication dispensing apparatus 104 may unlock the physical compartment 106 that stores the requested physical container 107 as instructed by the remote medication management system 102 (e.g., via an electronic signal electronically transmitted therefrom using a suitable communication channel). The input device that receives the user identifier for authentication and input device for the order for medication (e.g., medication identifier) can be the same or different and the inputs do not need to occur at the same time. That is the medication request may be put in from a remote terminal and the user ID at the device medication dispensing apparatus 104, as one example. The input devices can be a keypad, bar code scanner, RFID tag scanner, or nearly any suitable input device. The user may then access the physical container 107 to obtain the requested medication. In some cases, the display device 108 may be configured to display an indication of the physical container 107 that includes the medication requested by the user, such as by displaying a number or other symbol also displayed on the physical container, displaying a graphical representation of the physical compartment 106 and highlighting or otherwise indicating the physical container, or other suitable method. In some instances, the physical compartment 106 may be configured to indicate the physical container, such as by including lighting that emphasizes the physical container 107 therein that includes the requested medication.

The remote medication management system 102 may, as interfaced with the medication dispensing apparatus 104, be configured to detect the physical container 107 accessed by the user. For example, the remote medication management system 102 may detect the opening of a lid 109 of a physical container 109, such as via motion sensing, magnetics, or other suitable method, as an indication of access thereto by the user. The remote medication management system 102 may detect which physical container 107 is accessed, and may determine if the user accessed the correct physical container, where the correct physical container 107 may be the physical container 107 that includes the requested medication. If the correct physical container 107 is accessed, the display device 108 may request that the user withdraw the requested medication and scan the medication for confirmation. The medication may include a machine-readable code that may be read by an optical imager or other suitable input device interfaced with the remote medication management system 102 (e.g., or accessible thereto, such as via the medication dispensing apparatus 104) that is encoded with identification data, such as the medication identifier, that is communicated to the remote medication management system 102. For example, the medication dispensing apparatus 104 may include a bar code scanner that is used to scan a bar code on medication packaging to communicate a medication identifier to the remote medication management system 102.

If the correct (e.g., requested) medication is withdrawn from the physical container, the remote medication management system 102 may update the inventory of the physical container 107 to account for the withdrawal, and instruct the display device 108 to display that the correct medication was selected. If an incorrect medication was withdrawn (e.g., if the physical container 107 includes multiple medications and the wrong one was grabbed by the user), the remote medication management system 102 may instruct the display device 108 to display a message accordingly. In some cases, the remote medication management system 102 may initiate the same process as in the case of unauthorized access to a physical container, as discussed below. In other cases, the user may be instructed to return the incorrect medication and select the correct medication from the physical container.

If the remote medication management system 102 detects that an incorrect physical container 107 is accessed, then the remote medication management system 102 may instruct the medication dispensing apparatus 104 and/or other device or system interfaced therewith to initiate an alarm. The alarm may be visual (e.g., flashing lights), aural (e.g., a high-pitched siren), physical (e.g., vibration of the medication dispensing apparatus 104), or other suitable type or a combination thereof, which may indicate to the user that they accessed the incorrect, and thus an unauthorized, physical container. The remote medication management system 102 may instruct the display device 108 to display a message to the user requesting that the user re-inventory the physical container. The re-inventorying of the physical container 107 may include the scanning of each of the medications included in the physical container, where such data may be communicated to the remote medication management system 102. The remote medication management system 102 may update the container record for the physical container 107 accordingly, and may store an entry in an event log that corresponds to the unauthorized access.

The event log entry may include data associated with the user, such as the user's supplied authentication credentials or other data associated therewith (e.g., provided when registering, such as a name), as well as data associated with the inventory of the unauthorized physical container. For instance, the entry may include the inventory of the physical container 107 prior to the re-inventorying and after, or may include only any changes in the inventory of the physical container 107 after re-inventorying (e.g., or an indication that the inventory is unchanged, if applicable). In some cases, the entry may include additional information associated with the unauthorized access, such as a timestamp or, if the medication dispensing apparatus 104 is interfaced with a video capture device, an image of the user accessing the unauthorized physical container. In some embodiments, an event log may also be used to log entries related to all access to the medication dispensing apparatus 104, including instances where the proper physical container 107 and medication were accessed, such as for auditing, inventorying, and compliance purposes.

In some instances, the remote medication management system 102 may be configured to notify third parties when unauthorized access to a physical container 107 is performed. For instance, the remote medication management system 102 may be configured to electronically transmit an e-mail, short message service message, automated telephone call, or other type of message to a supervisor when unauthorized access is detected. Such a message may include the entry to the event log and/or data associated with the unauthorized access, which may be used by the supervisor accordingly. In such instances, the use of notifications may decrease the response time for contacting the user that performed the unauthorized access and decrease the time for auditing of the inventory of the remote medication management system 102 to ensure no theft or other misuse occurred with respect to the unauthorized access.

Once the user has finished accessing the medication dispensing apparatus 104, the user may return the physical compartment 106 to its initial position and close the cabinet, if applicable. The remote medication management system 102 may detect, via the medication dispensing apparatus 104, that the physical compartment 106 was returned to its initial position and may instruct the medication dispensing apparatus 104 to lock the physical compartment 106 (e.g., and cabinet, if applicable). The remote medication management system 102 may then wait for a new user and/or medication request and repeat the process discussed above for access thereto.

The methods and systems discussed herein may thus provide for a remote medication management system 102 that controls access to medications that provides for controlled access to medications to increase effectiveness of patient care and decrease theft and misuse, where monitoring and event logging techniques are used in conjunction therewith to provide such benefits without the need to mechanically lock every physical container 107 stored in a medication dispensing apparatus 104. As a result, the remote medication management system 102 may be significantly less expensive than alternative systems, and physical containers 107 may be re-inventoried and medications resupplied to the medication dispensing apparatus 104 faster and easier due to the absence of mechanical locks thereon. Thus, the remote medication management system 102 discussed herein may be at least as effective as traditional systems with respect to security, more effective with respect to maintenance, and less expensive.

Remote Medication Management System

Figure 2:
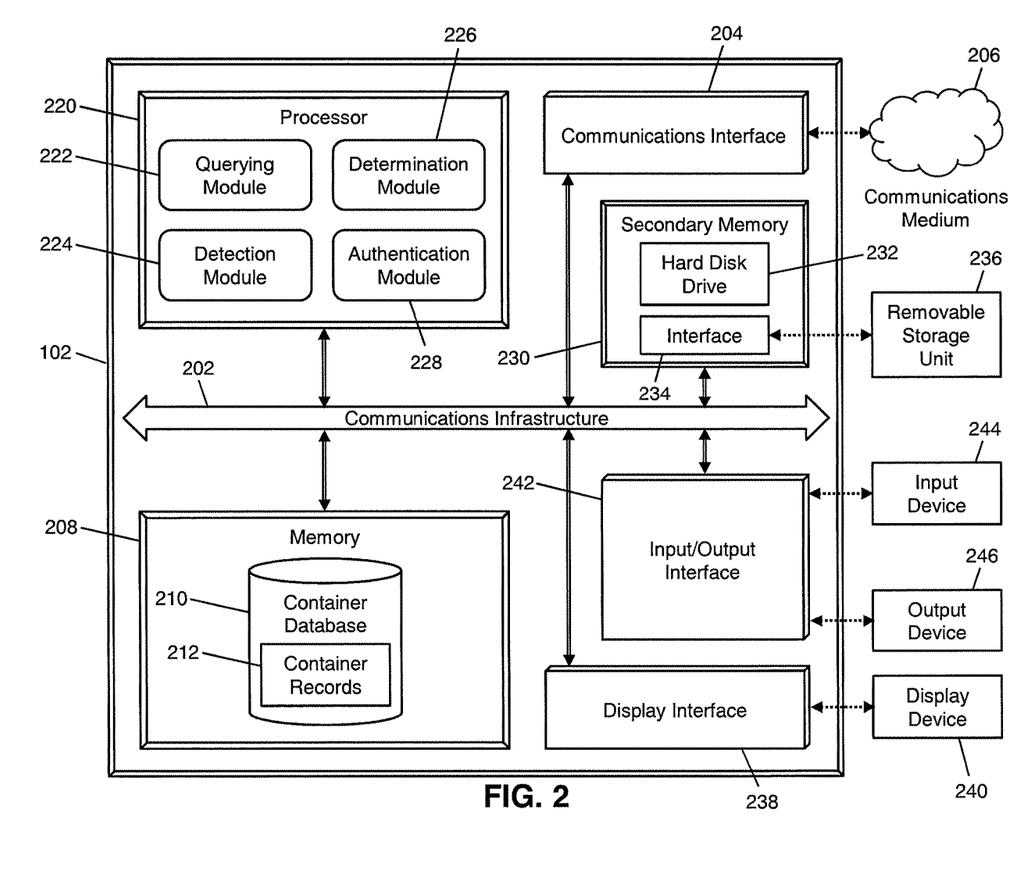
FIG. 2 is a block diagram illustrating the remote medication management system of FIG. 1A for the distributing, monitoring, and auditing of medication in accordance with exemplary embodiments.

FIG. 2 illustrates an embodiment of the remote medication management system 102 in the system 100. It will be apparent to persons having skill in the relevant art that the embodiment of the remote medication management system 102 illustrated in FIG. 2 is provided as illustration only and may not be exhaustive to all possible configurations of the remote medication management system 102 suitable for performing the functions as discussed herein.

The remote medication management system 102 may include a communications infrastructure 202. The communications infrastructure 202 may be configured to transmit data between modules, engines, databases, memories, and other components of the remote medication management system 102 for use in performing the functions discussed herein. The communications infrastructure 202 may be comprised of one or more communication types and utilize various communication methods for communications within a computing device. For example, the communications infrastructure 202 may be comprised of a bus, contact pin connectors, wires, etc. In some embodiments, the communications infrastructure 202 may also be configured to communicate between internal components of the remote medication management system 102 and external components of the remote medication management system 102, such as externally connected databases, display devices, input devices, etc.

The remote medication management system 102 may also include a communications interface 204. The communications interface 204 may include one or more interfaces used to interact with and facilitate communications between the remote medication management system 102 and one or more external devices via suitable communications mediums 206, such as to the medication dispensing apparatus 104. For instance, the communications interface 204 may interface with the communications infrastructure 202 and provide an interface 204 for connecting the remote medication management system 102 to one or more communications mediums 204 for the electronic transmission or receipt of data signals that are encoded or otherwise superimposed with data for use in performing the functions discussed herein. Communications interfaces 204 may include universal serial bus (USB) ports, Personal Computer Memory Card International Association (PCMCIA) ports, PS/2 ports, serial ports, fiber optic ports, coaxial ports, twisted-pair cable ports, wireless receivers, etc. Communications mediums 206 may include local area networks, wireless area networks, cellular communication networks, the Internet, radio frequency, Bluetooth, near field communication, etc.

In some instances, the remote medication management system 102 may include multiple communications interfaces 204 for electronically transmitting and receiving data signals via one or more communications mediums 206, such as a first communications interface 204 configured to transmit and receive data signals via a local area network and a second communications interface 204 configured to transmit and receive data signals via the Internet. In some instances, the communications interface 204 may include a parsing module for parsing received data signals to obtain the data superimposed or otherwise encoded thereon. For example, the communications interface 204 may include (e.g., or otherwise have access to, such as via the communications infrastructure 204) a parser program configured to receive and transform the received data signal into usable input for the functions performed by the processing device to carry out the methods and systems described herein.

The communications interface 204 may be configured to receive data signals electronically transmitted by medication dispensing apparatuses 104, which may be superimposed or otherwise encoded with signals indicating accessed physical containers 107 (e.g., identification values) and signals that include medication data read from scanned medication (e.g., medication identifiers). In some instances, the communications interface 204 may receive data signals superimposed with device identifiers from other computing devices, such as remote control that is interfaced with the remote medication management system 102 via the communications interface 204. The communications interface 204 may also be configured to electronically transmit data signals to medication dispensing apparatus 104, which may be superimposed or otherwise encoded with instructions regarding the locking and unlocking of the cabinet and, if applicable, individual physical compartments 106 for access thereto. In some instances, the communications interface 204 may be configured to electronically transmit data signals to and receive data signals from a display device 108 and input devices, such as to display notifications, alarms, and instructions, and to receive authentication credentials and medication requests.

The remote medication management system 102 may also include a memory 208. The memory 208 may be configured to store data for use by the remote medication management system 102 in perform the functions discussed herein. The memory 208 may be comprised of one or more types of memory using one or more suitable types of memory storage, such as random access memory, read-only memory, hard disk drives, solid state drives, magnetic tape storage, etc. The memory 208 may store data in any suitable type of configuration, such as in one or more lists, databases, tables, etc., which may store the data in a suitable data format and schema. In some instances, the memory 208 may include one or more relational databases, which may utilize structured query language for the storage, identification, modifying, updating, accessing, etc. of structured data sets stored therein.

The memory 208 of the remote medication management system 102 may include a container database 210. The container database 210 may be configured to store a plurality of container records 212 using a suitable storage format and schema. Each container record 212 may be a structured data set configured to store data related to a physical container 107 stored in the interfaced medication dispensing apparatus 104. Each container record 212 may include at least an identification value associated with the related physical container 107 and one or more inventory data entries. Each inventory data entry may be related to a medication stored in the related physical container 107 and include at least a medication identifier associated with the medication, and may also include additional data associated therewith, such as a quantity, dosage, medication name, etc. In some instances, a container record 212 may also include a compartment identifier, which may identify the physical compartment 106 in which the related physical container 107 is stored, such as for use in the unlocking thereof for access to the related physical container. In cases where the remote medication management system 102 may be interfaced with multiple medication dispensing apparatuses 104, the container record 212 may also indicate the medication dispensing apparatus 104 in which the physical container 107 is located.

In some embodiments, the memory 208 may also store data associated with users of the remote medication management system 102. For instance, the memory 208 may include a database of users and data associated therewith, such as access rules and permissions, authentication data, supervisor information, etc. Such data may be used for the authentication of users attempting to access the remote medication management system 102, determinations on rights of an authentication user to access a requested medication, and for logging actions performed by the user with respect to the access to and retrieval of medications in the medication dispensing apparatus 104.

The remote medication management system 102 may also include a processor 220. The processor 220 may be configured to perform the functions of the remote medication management system 102 discussed herein as will be apparent to persons having skill in the relevant art. In some embodiments, the processor 220 may include and/or be comprised of a plurality of engines and/or modules specially configured to perform one or more functions of the processing device, such as a querying module 222, detection module 224, determination module 226, authentication module 228, etc. As used herein, the term "module" may be software or hardware particularly programmed to receive an input, perform one or more processes using the input, and provides an output. The input, output, and processes performed by various modules will be apparent to one skilled in the art based upon the present disclosure. The processor 220 as discussed herein may be a single processor, a plurality of processors, or combinations thereof, which may also include processors that may have one or more processor "cores." Operations performed by the processor 220 or modules included therein may be performed as a sequential process and/or be performed in parallel, concurrently, and/or in a distributed environment. In some embodiments the order of operations may be rearranged without departing from the spirit of the disclosed subject matter. The processor 220 and the modules or engines included therein may be configured to execute program code or programmable logic to perform the functions discussed herein, such as may be stored in the memory 208 and/or a secondary memory 230, discussed in more detail below.

The processor 220 of the remote medication management system 102 may include a querying module 222. The querying module 222 may be configured to execute queries on databases to identify information. The querying module 222 may receive one or more data values or query strings, and may execute a query string based thereon on an indicated database, such as the container database 210, to identify information stored therein. The querying module 222 may then output the identified information to an appropriate engine or module of the remote medication management system 102 as necessary. The querying module 222 may, for example, execute a query on the container database 210 to identify a container record 212 that includes a medication identifier corresponding to one supplied in a medication request submitted by a user. The identified container record 212 may then be used to instruct the medication dispensing apparatus 104 to the appropriate physical compartment 106 for retrieval of the requested medication as stored therein.

The processor 220 of the remote medication management system 102 may also include a detection module 224. The detection module 224 may be configured to detect the opening of a physical container 107 in the medication dispensing apparatus using a suitable method associated therewith, such as motion detection, physical movement, change in state of an electrical connection using a mechanical switch or magnetic sensor that detects the opening and closing of the lid 109 on the container, etc. Detection of the opening of a physical container 107 may be performed via a communications interface 204 and associated communications medium 206 with the medication dispensing apparatus 104 in which the physical container 107 is located. The detection module 224 may detect the opening of a physical container 107 and identify the identification value of the physical container, which may be communicated to another module or engine of the processor 220 for use thereby. The detection module 224 may also be configured to detect the closing of physical containers 107 and/or physical compartments 106, such as for the locking of physical compartments 106 or the medication dispensing apparatus 104 once medications have been accessed.

The processor 220 of the remote medication management system 102 may further include a determination module 226. The determination module 226 may be configured to perform determinations for the remote medication management system 102, such as to determine if the correct physical container 107 was accessed for a medication request, if a user is authorized to access a requested medication, or if a physical compartment 106 and/or medication dispensing apparatus 106 should be closed. The determination module 226 may determine if a correct physical container 107 is being accessed based on identifying (e.g., via the issuing of an instruction to the querying module 222 and subsequent querying of the container database 210) if the inventory data entries included in a container record 212 for an opened physical container 107 include the medication identifier for a medication requested by the user. Authorized access to requested medications may be determined by the determination module 226 based on user access permissions and access data related to specific medications and/or physical containers 107 or physical compartments 106 based on data stored in the memory 208 of the remote medication management system 102. For instance, the determination module 226 may have to determine that a user is authorized access to not only a requested medication, but also to a physical container 107 that stores such medication. The determination module 226 may also be configured to determine when a locking or unlocking instruction should be issued to the medication dispensing apparatus 104, such as by ensuring that all requirements for unlocking have been met or ensuring that all physical containers 107 and compartments 106 have been closed prior to locking.

In some embodiments, the processor 220 of the remote medication management system 102 may also include an authentication module 228. The authentication module 228 may be configured to perform functions of the remote medication management system 102 related to the authentication of users. The authentication module 228 may be configured to register users for authentication using traditional methods, and may be configured to authenticate users of the remote medication management system 102 based on supplied authentication data and registered data, such as by comparing such data. For instance, the users may supply a fingerprint when requesting a medication, which may be compared to stored fingerprints by the authentication module 228 to determine who the user is and to identify the user's permissions for determination by the determination module 226 if the user is allowed access to a requested medication.

In some embodiments, the remote medication management system 102 may also include a secondary memory 230. The secondary memory 230 may be another memory in addition to the memory 208 that may be used to store additional data for use in performing the functions of the remote medication management system 102 as discussed herein. In some embodiments, the secondary memory 230 may be a different format or may use a different data storage method and/or schema than the memory 208. The secondary memory 230 may be any suitable type of memory, and, in some instances, may include multiple types of memory. For instance, the secondary memory 230 may be comprised of a hard disk drive 232 and one or more interfaces 234, where the interfaces 234 are configured to transmit data to and receive data from one or more removable storage units 236. Removable storage units 236 may include, for example, floppy disks, compact discs, digital video discs, Blu-ray discs, removable hard drives, flash drives, universal serial bus drives, etc.

In some cases, the remote medication management system 102 may also include a display interface 238. The display interface may be configured to interface the remote medication management system 102 with one or more display devices 240, such as display devices 108 interfaced directly with the remote medication management system 102 or the medication dispensing apparatus 104 (e.g., via the communications interface 204). The display devices 240 may be devices configure to display data received from the remote medication management system 102. Display devices 240 may be any suitable type of display, including, for example, liquid crystal displays, light emitting diode displays, thin film transistor display, capacitive touch displays, etc. In some instances, the remote medication management system 102 may include one or more display interfaces 238, which may interface with one or more display devices 240. Display devices 240 may, for example, display instructions, notifications, alarms, or other data received from the remote medication management system 102 for use in performing the functions discussed herein, such as for alarming when an unauthorized physical container 107 is accessed, illustrating which physical container 107 to access, instructing the user when to scan medications, requesting the user to close a physical compartment 106, etc.

The remote medication management system 102 may also include an input/output interface 242. The input/output interface 242 may be configured to interface the remote medication management system 102 with one or more input devices 244 and/or output devices 246 for the transmission to and receipt of data from the respective devices. The input/output interface 242 may include any suitable type of interface, and in some instances may include multiple types of interfaces, such as for interfacing with multiple types of input devices 244 and/or output devices 246. Input devices 244 may include any suitable type of device for inputting data to an remote medication management system 102, such as a keyboard, mouse, microphone, camera, touch screen, click wheel, scroll wheel, remote control, etc. Input devices 244 may be configured to receive input from a user of the remote medication management system 102, such as for the submission of a request for a medication, supplying of authentication credentials, reading of medication identifiers from medication, etc. Output devices 246 may include any suitable type of device for outputting data from the remote medication management system 102, such as a visual, aural, or physical alarm, speaker, remote control, headset, tactile feedback device, etc.

Process for Monitoring and Auditing Access to Medication

Figure 3:
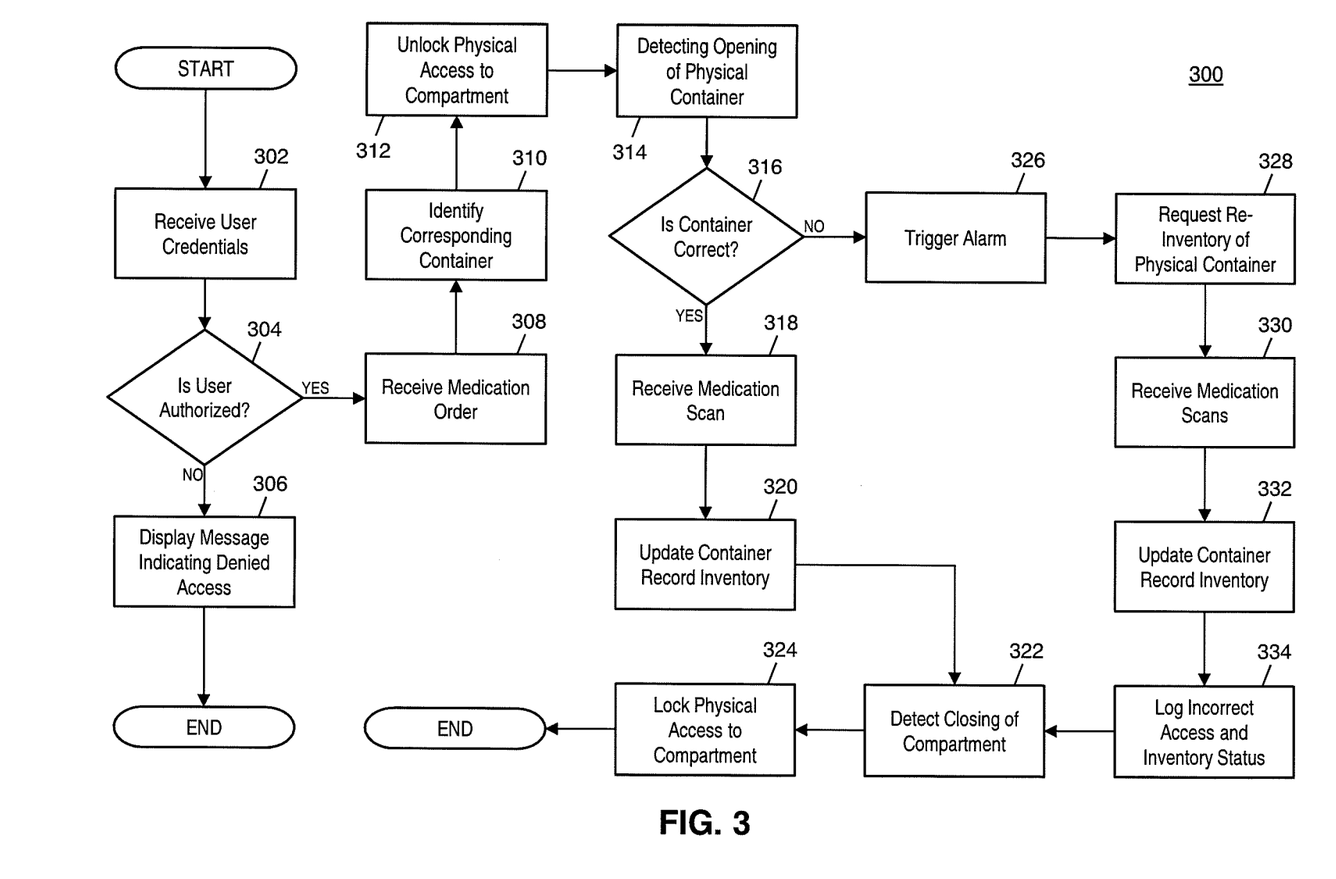
FIG. 3 is a flow diagram illustrating a process for the monitoring of remote access to medication using the remote medication management system of FIG. 2 in accordance with exemplary embodiments.

FIG. 3 illustrates a process 300 for the monitoring and auditing of access to medication stored in the medication dispensing apparatus 104 by the remote medication management system 102.

In step 302, the remote medication management system 102 may receive (e.g., via an input device 244) user credentials from a user thereof. In step 304, the determination module 226 of the remote medication management system 102 may determine if the user of the remote medication management system 102 is authorized for access to the interfaced medication dispensing apparatus 104. Such a determination may include identifying (e.g., via a query executed by the querying module 222 of the remote medication management system 102) if a user account is registered for the user based on their supplied authentication credentials. If no such account is identified, and thus the user is not authorized, then, in step 306, the remote medication management system 102 may instruct the display device 108 to display a message indicating that access to the medication dispensing apparatus 104 is denied. In some instances, the user may be requested to register with the remote medication management system 102 prior to repeating the process 300.

If a registered user account is identified that matches the authentication credentials supplied by the user, then, in step 308, the remote medication management system 102 may receive (e.g., via an input device 244) a medication order. The medication order may include at least a medication identifier associated with medication that is requested. The medication order may also include additional data associated with needed medication, such as an amount. For example, the medication order may be a request for four 325 milligram doses of aspirin. In step 310, the querying module 222 of the remote medication management system 102 may execute a query on the container database 210 to identify a container record 212 that includes an inventory data entry that includes the medication identifier for the requested medication. In instances where additional data may be included in the medication order, such as an amount, the query may also identify an appropriate container record 212 based thereon. For instance, in the above example, the querying module 222 may identify a container record 212 related to a physical container 107 that not only stores 325 milligram doses of aspirin, but that includes at least four such doses.

In step 312, the remote medication management system 102 may electronically transmit a data signal to the medication dispensing apparatus in which the physical container 107 related to the identified container record 212 is stored requesting that the medication dispensing apparatus 104 unlock the physical compartment 106 in which the physical container 107 is stored (e.g., as indicated in the container record 212). The medication dispensing apparatus 104 may then unlock access to the physical compartment 106 and provide access to the user to all physical containers 107 stored therein. In step 314, the detection module 224 of the remote medication management system 102 may detect the opening of a physical container 107 in the medication dispensing apparatus 104. As part of the detection, the detection module 224 may receive or otherwise identify an identification value associated with the opened physical container.

In step 316, the determination module 226 of the remote medication management system 102 may determine if the correct physical container 107 was opened. The correct physical container 107 may be the physical container 107 related to the identified container record 212, where such a determination may be based on the comparison of the identification value stored therein and an identification value received from the detection module 224 as a result of the detection. If the correct physical container 107 (e.g., the one identified in step 310) was opened, then, in step 318, the remote medication management system 102 may receive (e.g., via an input device 244) a medication scan. The medication scan may be a scan of the requested medication as performed by the user, such as by the use of a bar code scanner on a bar code displayed on packaging of the medication. The medication scan may include at least the medication identifier associated with the medication. In cases where multiple medications or amounts of a medication are withdrawn from the physical container, the medication scan may include multiple medication identifiers or multiple medication scans may be received. For instance, in the above example, the user may scan four separate 325 milligram doses of aspirin.

In step 320, the querying module 222 of the remote medication management system 102 may execute a query on the container database 210 to update the inventory data entries in the container record 212 for the physical container 107 to reflect the removal of the medication as indicated in the medication scan. For instance, in the above example, the querying module 222 may deduct four from the amount of 325 milligram doses of aspirin from the corresponding inventory data entry in the container record 212.

In step 322, the detection module 224 of the remote medication management system 102 may detect that the physical compartment 106 that had been unlocked is closed and able to be locked again. This may indicate to the remote medication management system 102 that the user has completed the withdrawal of the requested medication. In step 324, the remote medication management system 102 may electronically transmit a data signal to the medication dispensing apparatus 104 to request that the physical compartment 106 be locked or access thereto otherwise removed. Access to medications in the medication dispensing apparatus 104 may thus be prohibited until a new user authenticates with the remote medication management system 102 (e.g., in step 302) or a new medication order is received (e.g., in step 308), such as from the current user.

If, in step 316, the determination module 226 determines that an incorrect (e.g., unauthorized) physical container 107 was accessed, then, in step 326, the remote medication management system 102 may trigger an alarm. The alarm may be triggered via an instruction to the medication dispensing apparatus 104 or to a separate alarm device, and may be any suitable type of alarm that may indicate to the user that the incorrect physical container 107 was accessed. In step 328, the remote medication management system 102 may electronically transmit an instruction to the display device 108 to display an instruction to the user requesting that the physical container 107 be re-inventoried. In step 330, the remote medication management system 102 may receive medication scans for each of the medications stored in the physical container.

In step 332, the querying module 222 of the remote medication management system 102 may execute a query on the container database 210 to identify the container record 212 related to the incorrect physical container 107 based on the identification value and to update the inventory data entries stored therein based on the medication scans. In step 334, the incorrect accessing of the physical container 107 may be logged in an entry log, which may be stored locally in the remote medication management system 102 (e.g., in the memory 208, secondary memory 230, or other memory device) or in a separate computing system. The log for the incorrect access may include at least user data associated with the user and other data associated with the incorrect access, such as a timestamp, the identification value of the incorrect physical container, the medication order, and the inventory of the incorrect physical container 107 before and after the re-inventory and/or an indication of any changes in the physical container's inventory. In some embodiments, step 334 may include the electronic transmission of a data message related to the new log in the entry log, such as the transmission of an e-mail message to a supervisor of the user that includes the log. The process 300 may then proceed to step 322, where the closing of the physical compartment 106 may be detected and the physical compartment 106 locked. By this mechanism and process, individual locks on the physical containers 107 become unnecessary and can be omitted, though they could still be used for an additional safeguard or alternative reason in certain circumstances.

Exemplary Method for Monitoring Remote Access to Medication

Figure 4:
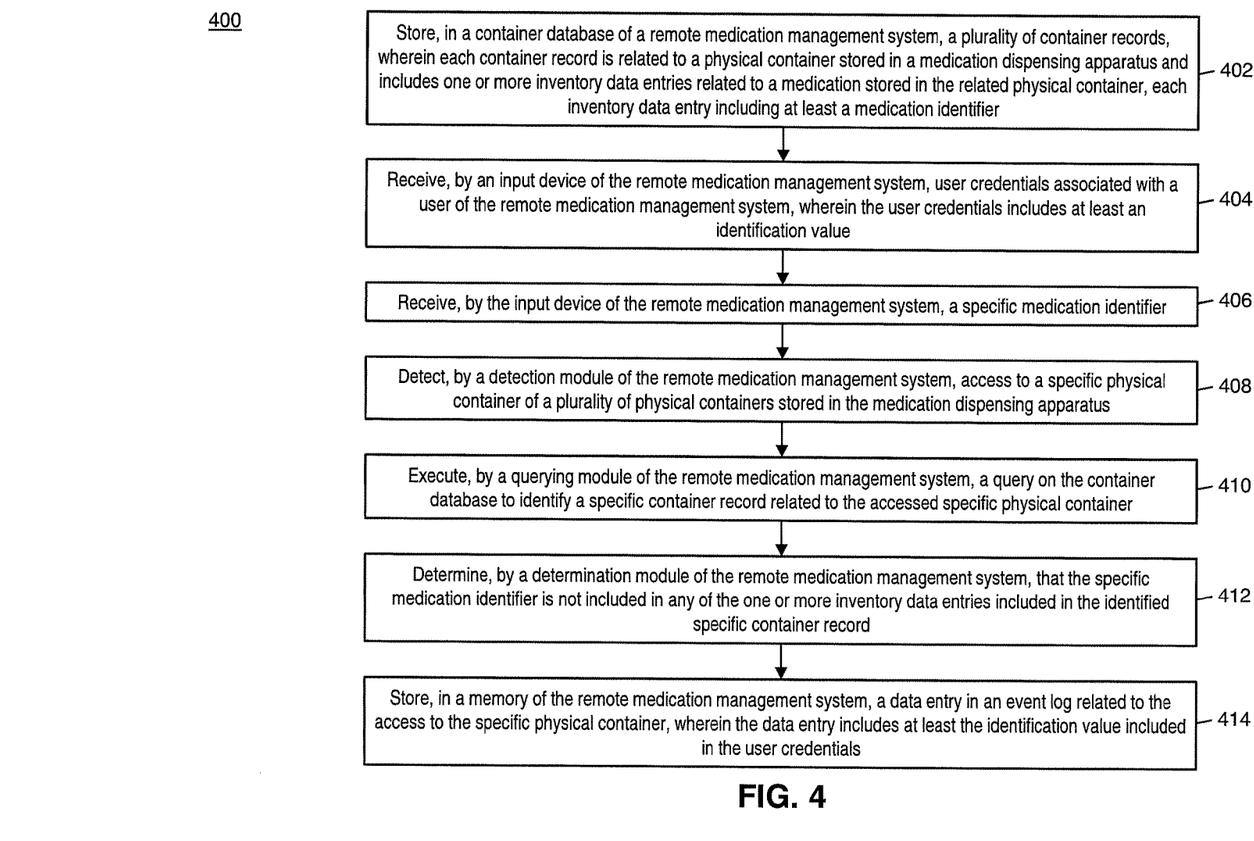
FIG. 4 is a flow chart illustrating an exemplary method for monitoring remote access to medication in accordance with exemplary embodiments.

FIG. 4 illustrates a method 400 for the monitoring of remote access to medication in a remote medication management system for the auditing thereof.

In step 402, a plurality of container records (e.g., container records 212) may be stored in a container database (e.g., the container database 210) of a remote medication management system (e.g., the remote medication management system 102), wherein each container record is related to a physical container 107 stored in a medication dispensing apparatus (e.g., the medication dispensing apparatus 104) and includes one or more inventory data entries related to a medication stored in the related physical container, each inventory data entry including at least a medication identifier. In step 404, user credentials associated with a user of the remote medication management system may be received by an input device (e.g., input device 244) of the remote medication management system, wherein the user credentials include at least an identification value.

In step 406, a specific medication identifier may be received by the input device of the remote medication management system. In step 408, access to a specific physical container 107 of a plurality of physical containers 107 stored in the medication dispensing apparatus may be detected by a detection module (e.g., the detection module 224) of the remote medication management system. In step 410, a query may be executed on the container database by a querying module (e.g., the querying module 222) of the remote medication management system to identify a specific container record related to the accessed specific physical container.

In step 412, a determination may be made by a determination module (e.g., the determination module 226) of the remote medication management system that the specific medication identifier is not included in any of the one or more inventory data entries included in the identified specific container record. In step 414, a data entry may be stored in an event log in a memory (e.g., the memory 208) of the remote medication management system related to the access to the specific physical container, wherein the data entry includes at least the identification value included in the user credentials.

In one embodiment, the data entry may further include at least the specific medication identifier and data identifying the accessed specific physical container. In some embodiments, the method 400 may also include electronically transmitting, by a transmitting device (e.g., the communications interface 204) of the remote medication management system, a signal to the medication dispensing apparatus to unlock a cabinet providing access to the specific physical container.

In one embodiment, the method 400 may further include electronically transmitting, by the transmitting device of the remote medication management system, a signal to the medication dispensing apparatus to activate an alarm of the medication dispensing apparatus. In a further embodiment, activation of the alarm may include displaying, on a display device (e.g., the display device 108) interfaced with the medication dispensing apparatus, an instruction to the user to re-inventory the accessed specific physical container.

In some embodiments, the method 400 may further include: receiving, by the input device of the remote medication management system, one or more medication identifiers; and executing, by the querying module of the remote medication management system, a second query on the container database to update the one or more inventory data entries included in the specific container record based on the received one or more medication identifiers. In a further embodiment, the data entry may further include any changes between the one or more inventory data entries included in the specific container record before and after the update.

In one embodiment, the medication dispensing apparatus may include a plurality of separated physical compartments (e.g., physical compartments 106), and each container record may include an associated physical compartment related to one of the plurality of separated physical compartments housing the related physical container. In a further embodiment, the method 400 may also include: executing, by the querying module of the remote medication management system, a query on the container database to identify a desired container record where the medication identifier included in one of the included one or more inventory data entries corresponds to the specific medication identifier; and electronically transmitting, by the transmitting device of the remote medication management system, a signal to the medication dispensing apparatus to unlock the associated physical compartment indicated in the identified desired container record. In an even further embodiment, the desired container record and specific container record may include a common associated physical compartment.

Techniques consistent with the present disclosure provide, among other features, systems and methods for monitoring remote access to medication. While various exemplary embodiments of the disclosed system and method have been described above it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope.

What is claimed is:

1. A method for monitoring remote access to medication, comprising:

storing, in a container database of a remote medication management system, a plurality of container records, wherein each container record is related to a physical container stored in a medication dispensing apparatus and includes an associated physical compartment that houses the related physical container and one or more inventory data entries related to a medication stored in the related physical container, each inventory data entry including at least a medication identifier, where the medication dispensing apparatus includes a plurality of separated physical compartments;

receiving, by an input device of the remote medication management system, user credentials associated with a user of the remote medication management system, wherein the user credentials includes at least an identification value;

receiving, by an input device of the remote medication management system, a specific medication identifier;

executing, by a querying module of the remote medication management system, a query on the container database to identify a desired container record where the medication identifier included in one of the included one or more inventory data entries corresponds to the specific medication identifier;

electronically transmitting, by a transmitting device of the remote medication management system, a signal to the medication dispensing apparatus to unlock the associated physical compartment indicated in the identified desired container record;

detecting, by a detection module of the remote medication management system, access to a specific physical container of a plurality of physical containers stored in the medication dispensing apparatus;

executing, by the querying module of the remote medication management system, a query on the container database to identify a specific container record related to the accessed specific physical container;

determining, by a determination module of the remote medication management system, that the specific medication identifier is not included in any of the one or more inventory data entries included in the identified specific container record of the container detected by the detection module; and storing, in a memory of the remote medication management system, a data entry in an event log related to the access to the specific physical container, wherein the data entry includes at least the identification value included in the user credentials.

2. The method of claim 1, wherein the data entry further includes at least the specific medication identifier and data identifying the accessed specific physical container.

3. The method of claim 1, further comprising:
electronically transmitting, by a transmitting device of the remote medication management system, a signal to the medication dispensing apparatus to activate an alarm of the medication dispensing apparatus.

4. The method of claim 3, wherein activation of the alarm includes displaying, on a display device interfaced with the medication dispensing apparatus, an instruction to the user to re-inventory the accessed specific physical container.

5. The method of claim 1, further comprising:
receiving, by the input device of the remote medication management system, one or more medication identifiers; and executing, by the querying module of the remote medication management system, a second query on the container database to update the one or more inventory data entries included in the specific container record based on the received one or more medication identifiers.

6. The method of claim 5, wherein the data entry further includes any changes between the one or more inventory data entries included in the specific container record before and after the update.

7. The method of claim 1, further comprising:
electronically transmitting, by a transmitting device of the remote medication management system, a signal to the medication dispensing apparatus to unlock a cabinet providing access to the specific physical container.

8. The method of claim 1, wherein the desired container record and specific container record include a common associated physical compartment.

9. A remote medication management system for monitoring remote access to medication interfaced with a medication dispensing apparatus, comprising:
a container database storing a plurality of container records, wherein each container record is related to a physical container stored in the medication dispensing apparatus and includes an associated physical compartment that houses the related physical container and one or more inventory data entries related to a medication stored in the related physical container, each inventory data entry including at least a medication identifier, where the medication dispensing apparatus includes a plurality of separated physical compartments;

an input device
receiving user credentials associated with a user of the remote medication management system, wherein the user credentials includes at least an identification value, and
receiving a specific medication identifier;

a querying module executing a query on the container database to identify a desired container record where the medication identifier included in one of the included one or more inventory data entries corresponds to the specific medication identifier;

a transmitting device transmitting a signal to the medication dispensing apparatus to unlock the associated physical compartment indicated in the identified desired container record;

a detection module detecting access to a specific physical container of a plurality of physical containers stored in the medication dispensing apparatus;

a determination module; and a memory module, wherein the querying module further executes a query on the container database to identify a specific container record related to the accessed specific physical container;

the determination module determines that the specific medication identifier is not included in any of the one or more inventory data entries included in the identified specific container record of the container detected by the detection module; and the memory stores a data entry in an event log related to the access to the specific physical container, wherein the data entry includes at least the identification value included in the user credentials.

10. The remote medication management system of claim 9, wherein the data entry further includes at least the specific medication identifier and data identifying the accessed specific physical container.

11. The remote medication management system of claim 9, further comprising:
a transmitting device transmitting a signal to the medication dispensing apparatus to activate an alarm of the medication dispensing apparatus.

12. The remote medication management system of claim 11, wherein activation of the alarm includes displaying, on a display device interfaced with the medication dispensing apparatus, an instruction to the user to re-inventory the accessed specific physical container.

13. The remote medication management system of claim 9, wherein
   the input device further receives one or more medication identifiers, and
   the querying module further executes a second query on the container database to update the one or more inventory data entries included in the specific container record based on the received one or more medication identifiers.

14. The remote medication management system of claim 13, wherein the data entry further includes any changes between the one or more inventory data entries included in the specific container record before and after the update.

15. The remote medication management system of claim 9, further comprising:
   a transmitting device transmitting a signal to the medication dispensing apparatus to unlock a cabinet providing access to the specific physical container.

16. The remote medication management system of claim 9, wherein the desired container record and specific container record include a common associated physical compartment.

* * * * *